United States Patent [19]

Shiraga et al.

[11] Patent Number: 4,888,417

[45] Date of Patent: Dec. 19, 1989

[54] THERAPEUTIC AND PROPHYLACTIC AGENTS FOR PEPTIC ULCER

[75] Inventors: Yusei Shiraga, Hyogo; Chikara Fukaya; Toshiaki Akira, both of Osaka; Masakazu Iwai; Kazumasa Yokoyama, both of Osaka; Mamoru Tabata, Kyoto; Hiroshi Fukui, Shiga; Shigeo Tanaka, Kyoto; Yoshiro Iga, Osaka; Tadakazu Suyama, Kyoto; Kanemichi Okano, Osaka, all of Japan

[73] Assignee: Green Cross Corporation, Osaka, Japan

[21] Appl. No.: 867,169

[22] Filed: May 27, 1986

[30] Foreign Application Priority Data

May 25, 1985 [JP] Japan .................. 60-112836
May 25, 1985 [JP] Japan .................. 60-112837
May 25, 1985 [JP] Japan .................. 60-112838
Oct. 21, 1985 [JP] Japan .................. 60-234739

[51] Int. Cl.[4] ............................................. A61K 31/70
[52] U.S. Cl. .................... 536/4.1; 424/195.1; 514/927
[58] Field of Search ............. 424/195.1; 514/927; 536/4.1

[56] References Cited

U.S. PATENT DOCUMENTS

| | | | |
|---|---|---|---|
| 4,235,889 | 11/1980 | Evers | 514/861 |
| 4,402,950 | 9/1983 | Wolf et al. | 424/195.1 |
| 4,409,245 | 10/1983 | Wolf et al. | 426/9 |
| 4,618,495 | 10/1986 | Okuda et al. | 424/195.1 |
| 4,732,760 | 3/1988 | Iga et al. | 514/925 |

FOREIGN PATENT DOCUMENTS 2901829 8/1979 Fed. Rep. of Germany .

OTHER PUBLICATIONS

PATENT ABSTRACTS OF JAPAN, vol. 8, No. 162, (C—235) (1599), Jul 26, 1984; & JP—A—59 65018 (MIDORI JUJI) 13-04-1984.

*Primary Examiner*—Ronald W. Griffin
*Attorney, Agent, or Firm*—Sughrue, Mion, Zinn, Macpeak & Seas

[57] ABSTRACT

A therapeutic and prophylactic agent for peptic ulcers which contains as an active ingredient a compound of the general formula (I):

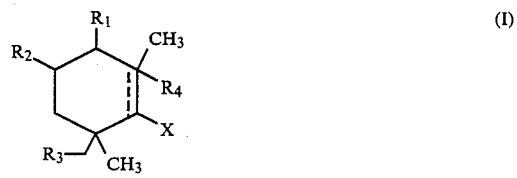

wherein $R_1$ represents hydrogen or $=O$; $R_2$ represents hydrogen or $-OR_5$; $R_3$ represents hydrogen or $-OR_6$; $R_4$ represents $-OR_7$ in the case of the absence of double bond; $R_5$, $R_6$ and $R_7$ each represents hydrogen or an organic residue;

X represents group (A):

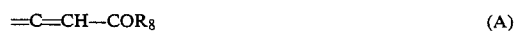

or group (B):

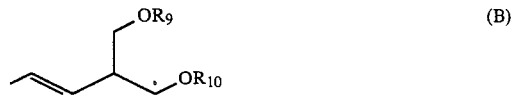

wherein $R_8$ represents alkyl, and $R_9$ and $R_{10}$ each represents hydrogen or an organic residue; with the proviso that when X represents group (A), then $R_1$ and $R_3$ both represent hydrogen, $R_2$ represents $-OR_5$; $R_4$ represents $OR_7$ and the bond between the carbon atoms to which X is attached and the carbon atom to which $R_4$ is attached is a single bond, and when X represents group (B), then $R_1$ represents $=O$, $R_2$ represents hydrogen, $R_3$ represents $-OR_6$ and the bond between the carbon atom to which X is attached and the carbon atom to which $R_4$ is attached is a double bond, or a pharmaceutically acceptable salt thereof, or a compound of the general formula (II):

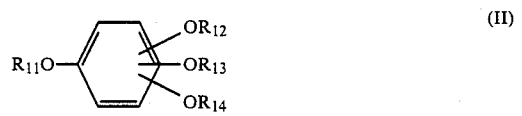

wherein $R_{11}$ represents hydrogen or an organic residue, and $R_{12}$, $R_{13}$ and $R_{14}$ each represents an organic residue, or a pharmaceutically acceptable salt thereof. The compounds of the general formulae (I) and (II) can be derived from compounds contained in a hot water extract of cinnamon.

9 Claims, No Drawings

THERAPEUTIC AND PROPHYLACTIC AGENTS FOR PEPTIC ULCER

FIELD OF THE INVENTION:

This invention relates to novel therapeutic and prophylactic agents for peptic ulcer, a process for the production thereof and pharmaceutical compositions having anti-ulcer activity.

BACKGROUNDS OF THE INVENTION

While various types of compounds have heretofore been known as therapeutic and prophylactic agents for peptic ulcers it has become an important subject to develop novel therapeutic and prophylactic agents since ulcers have lately shown an increasing trend.

It is known that a water-soluble fraction derived from cinnamon (a plant belonging to the family Lauraceae) has anti-ulcer activity (Japanese Patent Application (OPI) No. 65018/84. That is, by screening the pharmacological effect of this water-soluble fraction contained in cinnamon, it has been discovered that the water-soluble fraction has a strong effect on the inhibition of gastric secretions, increases the blood circulation in the gastric mucous membrane, promotes the gastric mucus and promotes the restraining of the gastric mucous membrane. The ability to inhibit gastric secretions is comparable to or better than that of Cimetidine, which is presently regarded as the strongest known anti-ulcer agent. Moreover, the cinnamon-derived water soluble fraction also has a prophylactic effect against stress ulcers and serotonin induced ulcers.

SUMMARY OF THE INVENTION

An object of this invention is to provide novel compounds having peptic anti-ulcer activity.

Another object of this invention is to provide a process for the production of novel compounds having peptic anti-ulcer activity.

Still another object of this invention is to provide pharmaceutical compositions having peptic anti-ulcer activity.

The above-described objects have been met based on the finding in the present invention that above-described cinnamon-derived water-soluble fraction contains an anti-ulcer active component, which has been extracted, isolated, and identified for the first time in the present invention. It has been found in the present invention that various derivatives of this active component have anti-ulcer activity.

According to one embodiment, this invention relates to a novel compound of the general formula (I):

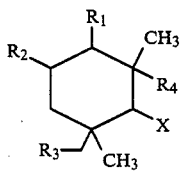
(I)

wherein $R_1$ represents hydrogen or $=O$; $R_2$ represents hydrogen or $-OR_5$; $R_3$ represents hydrogen or $-OR_6$; $R_4$ represents $-OR_7$ in the case of the absence of double bond, $R_5$, $R_6$ and $R_7$ each represents hydrogen or an organic residue;

X represents groups (A):

$$=C=CH-COR_8 \quad (A)$$

or group (B):

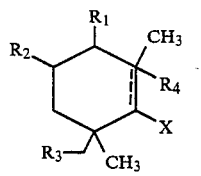
(B)

wherein $R_8$ represents alkyl, and $R_9$ and $R_{10}$ each represents hydrogen or an organic residue; with the proviso that when X represents groups (A), then $R_1$ and $R_3$ both represent hydrogen, $R_2$ represents $-OR_5$, $R_4$ represents $OR_7$ and the bond between the carbon atom to which X is attached and the carbon atom to which $R_4$ is attached is a single bond, and when X represents group (B), then $R_1$ represents $=O$, $R_2$ represents hdyrogen, $R_3$ represents $-OR_6$ and the bond between the carbon atom to which X is attached and the carbon atom to which $R_4$ is attached is a double bond.

According to another embodiment, this invention provides a process for the production of a novel compound of the general formula (I):

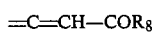
(I)

wherein $R_1$ represents hydrogen or $=O$; $R_2$ represents hydrogen or $-OR_5$; $R_3$ represents hydrogen or $-OR_6$; $R_4$ represents $-OR_7$ in the case of the absence of double bond, $R_5$, $R_6$ and $R_7$ each represents hydrogen or an organic residue;

X represents group (A):

$$=C=CH-COR_8 \quad (A)$$

or group (B):

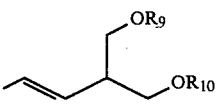
(B)

wherein $R_8$ represents alkyl and $R_9$ and $R_{10}$ each represents hydrogen or an organic residue; with the proviso that when X represents groups (A), then $R_1$ and $R_3$ both represent hydrogen, $R_2$ represents $-OR_5$, $R_4$ represents $OR_7$ and the bond between the carbon atom to which X is attached and the carbon atom to which $R_4$ is attached is a single bond, and when X represents group (B), then $R_1$ represents $=O$, $R_2$ represents hydrogen, $R_3$ represents $-OR_6$ and the bond between the carbon atom to which X is attached and the carbon atom to which $R_4$ is attached is a double bond.

Further, according to still another embodiment, this invention also provides a therapeutic and prophylactic agent for peptic ulcer which contains a compound of the general formula (I):

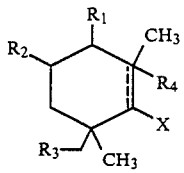

wherein $R_1$ represents hydrogen or $=O$; $R_2$ represents hydrogen or $-OR_5$; $R_3$ represents hydrogen or $-OR_6$; $R_4$ represents $-OR_7$ in the case of absense of double bond; $R_5$, $R_6$ and $R_7$ each represents hydrogen or an organic residue;

X represents group (A):

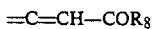

or group (B):

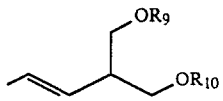

wherein $R_8$ represents alkyl, and $R_9$ and $R_{10}$ each represents hydrogen or an organic residue; with the proviso that when X represents group (A), then $R_1$ and $R_3$ both represent hydrogen, $R_2$ represents $-OR_5$, $R_4$ represents $OR_7$ and the bond between the carbon atom to which X is attached and the carbon atom to which $R_4$ is attached is a single bond, and when X represents group (B), then $R_1$ represents $=O$, $R_2$ represents hydrogen, $R_3$ represents $-OR_6$ and the bond between the carbon atom to which X is attached and the carbon atom to which $R_4$ is attached is a double bond, and a compound of the general formula (II):

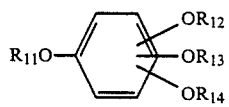

wherein $R_{11}$ represents hydrogen or an organic residue, and $R_{12}$, $R_{13}$ and $R_{14}$ each represents an orgnic residue or at least one of pharmaceutically acceptable salt of each of compound (I) and (II) as active ingredients and a pharmaceutically acceptable carrier, and process for the production thereof.

DETAILED DESCRIPTION OF THE INVENTION

In the compound of the general formula (I), when X represents group (A), the compound (I) is a compound of the general formula (III):

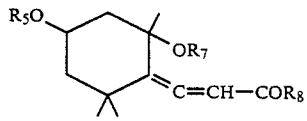

wherein $R_5$, $R_7$ and $R_8$ are as defined above under the general formula (I), and when X represents group (B), the compound (I) is a compound of the general formula (IV):

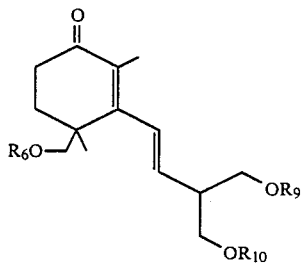

wherein $R_6$, $R_9$ and $R_{10}$ are as defined above under the general formula (I).

The organic residue in the present specification is not particularly restricted as long as it is pharmacologically acceptable. Example of such organic residues include the following groups;

For $R_5$, $R_6$, $R_9$ and $R_{10}$, oligosaccharide residues of 1 to 3 saccharide units, alkyl, acyl, alkoxycarbonyl, alkoxycarbonylalkyl, carboxyalkyl, carboxyalkylcarbonyl, cyclic acetal, etc. may be illustrated. For $R_7$, alkyl, acyl, alkoxycarbonyl, alkoxycarbonylalkyl, carboxyalkyl, carboxyalkylcarbonyl, cyclic acetal, etc. may be illustrated. For $R_{11}$, hydrogen, oligosaccharide residues of 1 to 3 saccharide units, lower alkyl, acyl, alkoxycarbonyl, alkoxycarbonylalkyl carboxyalkyl, carboxyalkylcarbonyl, etc. may be illustrated. For $R_{12}$, $R_{13}$ and $R_{14}$, alkyl, acyl, alkoxycarbonyl, alkoxycarbonylalkyl, carboxyalkyl, carboxyalkylcarbonyl, etc. may be illustrated.

In this specification, the alkyl is preferably that of 1 to 6 carbon atoms, in particular, 1 to 4 carbon atoms, which may be either straight-chain or branched-chain, and specific examples thereof include methyl, ethyl, n-propyl, iso-propyl, n-butyl, t-butyl, n-pentyl, etc. The alkoxy is preferably that of 1 to 6 carbon atoms, in particular, 1 to 3 carbon atoms, which may be either straight-chain or branched chain, and specific examples thereof include methoxy, ethoxy, n-propoxy, iso-propoxy, n-butoxy, t-butoxy, etc., and further the acyl may be either aliphatic or aromatic, the aliphatic type being illustrated by those of 1 to 6 carbon atoms, in particular 2 to 5 carbon atoms, such as acetyl, propionyl, butyryl, valeryl, etc., and the aromatic type being illustrated by benzoyl, etc.

Further, the alkoxy moiety of the alkoxycarbonyl is as described above, and said group is illustrated by for example methoxycarbonyl, ethoxycarbonyl, etc. The alkoxy moiety and the alkyl moiety in the alkoxycarbonylalkyl are as described above, and said group is illustrated by for example methoxycarbonylmethyl, etc. The alkyl moiety in the carboxyalkyl is as described above, and said group is illustrated by for example carboxymethyl, etc. The alkyl moiety in the carboxyalkylcarbonyl is as described above, and said group is illustrated by for example carboxyethylcarbonyl, etc. The cyclic acetal is illustrated by, for example, tetrahydropyranyl, etc.

Further, the oligosaccharide residue of 1 to 3 saccharide units means a mono-, di- or triglycoside residue. The constituting saccharides are not particularly restricted. Examples of the monoglycoside residue include glucosyl, arabinosyl, galactosyl, mannosyl, fructosyl, xylosyl, ribosyl, apiosyl, glucosamine groups, etc.; examples of the diglycoside residue include apiosylglucosyl, sucrosyl, maltosyl, lactosyl, gentiobiosyl groups, etc.; and examples of the triglycoside residue include apiosylgentiobiosyl, gentianosyl, raffinosyl groups, etc. The hydroxyl groups in these saccharide moieties may partially or wholly be substituted with lower alkyl, acyl, alkoxycarbonyl, alkoxycarbonylalkyl, carboxyalkyl, carboxyalkylcarbonyl or cyclic acetal.

The compounds (I) or (II) may be produced for example as follows:

First, a cinnamon-derived water-soluble fraction is prepared by a known process (e.g. Japanese Patent Application (OPI) No. 65018/84). That is, ethyl ether is added to a hot water extract of cinnamon, which is then subjected to partition fractionation and the water-soluble fraction is recovered.

The temperature of the hot water extract is preferably about 100° C., and the extraction is about 1 to 4 hours, in particular about 2 hours being preferred. Said extract is preferably concentrated on a warm bath to about 0.1 to 0.4%, in particular to about 0.2%, before the partition fractionation with ethyl ether. The thus obtained extract (concentrated solution) is then subjected to counter-current partition fractionation, and, on that occasion, ethyl ether is preferably used in an equivalent amount to said extract.

The hot water extract fraction of cinnamon is fractionated by employing in combination as appropriate, normal phase adsorption chromatography (silica gel, activated alumina, etc. as a packed solid; chloroform+methanol, chloroform+methanol+water, ethyl acetate+ethanol+water, hexane+acetone, etc. as an eluting solvent), reversed phase partition chromatography ($C_{18}$ (octadecylsilane), $C_8$ (octylsilane), etc. as a packed solid; methanol+water, acetonitrile+water, tetrahydrofuran+water, etc. as an eluting solvent), and other chromatography (Amberlite XAD-2, etc. as a packed solid; methanol+water, etc. as an eluting solvent), thereby the following three compounds (II-1), (III-1) and (IV-1) can be obtained.

the compounds (II-1) of the formula:

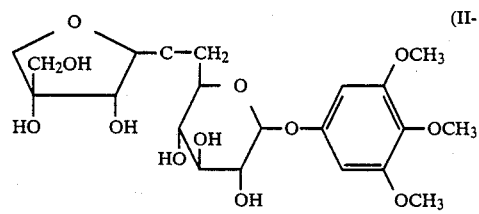

the compounds (III-1) of the formula:

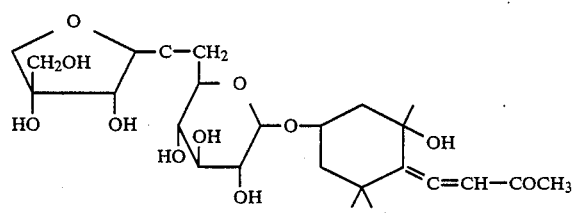

the compounds (IV-1) of the formula:

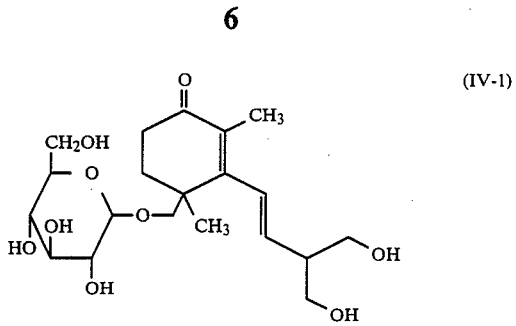

The compound (II-1) can be hydrolyzed in a conventional manner (e.g., T. Hase and T. Imagawa, Bull Chem. Soc. Jpn, 55, 3663 (1982)) to obtain a compound of the formula (II-2):

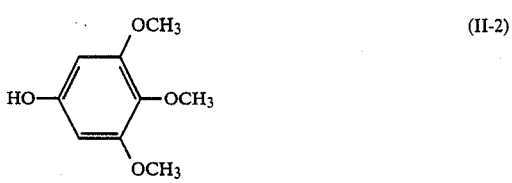

Said compound (II-2) can be converted to a compound of the formula (II-3):

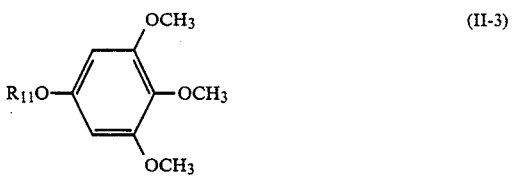

wherein $R_{11}$ is as defined above by reacting with, e.g., a compound of the general formula (V):

$R_{11}$—Br (V)

wherein $R_{11}$ is defined above.

The compound (II-2) can be hydrolyzed in a conventional manner (e.g., K. E. Hamlin and F. E. Fischer, J. Amer. Chem. Soc. Jpn., 75, 5119 (1953)) to obtain a compund of the formula (II-4):

(II-4)

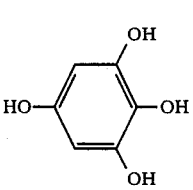

and thereafter reacted with e.g. a compound of the general formula (VI) or (VII):

$$R_{15}-Y \quad (VI)$$

$$R_{15}-O-Y' \quad (VII)$$

wherein $R_{15}$ is as defined above for $R_{12}$, $R_{13}$ and $R_{14}$, and Y and Y' each represents a reactive substituent (e.g. halogen, etc. for Y and p-toluenesulfonyl, methanesulfonyl, etc. for Y') to obtain a compound of the formula (II-5):

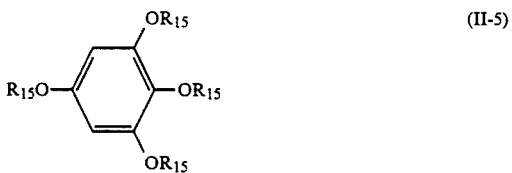

wherein $R_{15}$ is as defined above.

The compound (III-1) can be hydrolyzed in a conventional manner (e.g., T. Imagawa and T. Hase, Phytochem., 22, 255 (1983)) to obtain a compound of the formula (III-2):

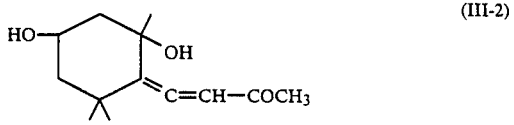

Said compound (III-1) or compound (III-2) can be derived in a conventional manner such as acetylation, methylation as described in T. Imagawa and T. Hase, Phytochem., 22, 255 (1983) to produce another compound (III).

For example, an oligosaccharide derivative of the compound (III-2) can be produced by reacting an activated glycoside (e.g. bromoglycoside), etc. upon the compound (III). The reaction is preferably carried out in the presence of a solvent inert to the reaction (e.g. chloroform, dichloromethane, tetrahydrofuran, etc.), the reaction temperature is preferably about 0° to 80° C., and the reaction time is preferably about 0.5 to 5 hours.

Further, the compound (III-1) can be treated by a known method (e.g., D. Dess, H. P. Kleine, D. V. Weinberg, R. J. Kauffman, K. S. Sidhu, Synthesis, 883 (1981) and H. Paulsen, Angew. Chem. Int. Ed. Eng., 21, 155 (1982)) to produce a compound of the general formula (III-3):

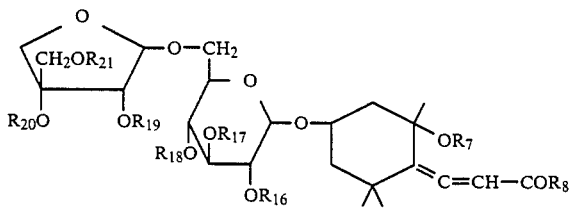

wherein $R_7$ and $R_8$ are as defined above, and $R_{16}$, $R_{17}$, $R_{18}$, $R_{19}$, $R_{20}$ and $R_{21}$ each represents an organic residue, preferably alkyl, acyl, alkoxycarbonyl, alkoxycarbonylalkyl, carboxyalkyl, carboxyalkylcarbonyl, cyclic acetal, etc.

For example, in the compound (III-3), the compound wherein $R_8$ is methyl and $R_7$, $R_{16}$, $R_{17}$, $R_{18}$, $R_{19}$, $R_{20}$ and $R_{21}$ are each alkyl can be produced by alkylating the compound (III-1) in a conventional manner (e.g., T. Imagawa and T. Hase, Phytochem., 22, 255 (1983)).

The alkylating agent for said alkylation is illustrated preferably by halogenated alkyls (e.g. methyl iodide, etc.), alkyl sulfates (e.g. dimethyl sulfate), etc. The alkylation is preferably carried out in the presence of a solvent inert to the reaction (e.g. acetone, chloroform, dichloromethane, tetrahydrofuran, dimethyl sulfoxide, N,N-dimethylformamide, etc.) and also in the presence of a base (e.g. sodium hydride, silver oxide, potassium carbonate, sodium carbonate, etc.). The reaction time is about 0.5 to 5 hours, and the reaction temperature is about 0° to 80° C.

The compound wherein $R_8$ is methyl and $R_7$, $R_{16}$, $R_{17}$, $R_{18}$, $R_{19}$, $R_{20}$ and $R_{21}$ are each acyl can be produced by acylating the compound (III-1). The acylating agent in said acylation is illustrated preferably by known compounds such as reactive derivatives, acid halides (e.g., acid chlorides, acid bromides, etc.) acid anhydrides, active esters, etc. Where the carboxylic acid is used as the acylating agent, it is preferred to carry out the reaction in the presence of a condensing agent, for example, dicyclohexylcarbodiimide, etc. Alternatively, where other acylating agents are used, the acylation is preferably carried out in the presence of a tertiary amine such as pyridine, triethylamine, etc. In either case, a solvent inert to the reaction (chloroform, dichloromethane, tetrahydrofuran, etc.) can also be safely present. The reaction time is about 0.5 to 5 hours and the reaction temperature is about 0°-25° C.

The compound (IV-1) can be treated with glycosidase to obtain a compound of the formula (IV-2):

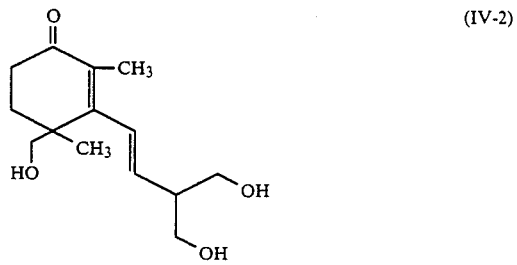

and thereafter it can be derived by a conventional manner (e.g., T. Imagawa and T. Hase, Phytochem., 22, 255 (1983)) to obtain another compound (IV) of this invention.

For example, the compound (IV) wherein $R_6$, $R_9$ and $R_{10}$ are each alkyl can be produced by alkylating the compound (IV-2). The alkylating agent in said alkylation is illustrated preferably by halogenated alkyls (e.g. methyl iodide, etc.), alkyl sulfates (e.g. dimethyl sulfate), etc. The alkylation is preferably carried out in the presence of a solvent inert to the reaction (e.g. acetone, chloroform, dichloromethane, tetrahydrofuran, dimethylsulfoxide, N,N-dimethylformamide) and also in the presence of a base (e.g. sodium hydride, silver oxide, potassium carbonate, sodium carbonate, etc.). The reaction time is about 0.5 to 5 hours, and the reaction temperature is about 0° to 80° C.

Further, the compound (IV) wherein $R_6$, $R_9$ and $R_{10}$ are each acyl can be produced by acylating the compound (IV-2). The acylating agent in said acylation is preferably a carboxylic acid and reactive derivatives thereof. Said reactive derivatives are illustrated by known compounds such as acyl halides (e.g. acid chlorides, acid bromides), acid anhydrides, active esters, etc. Where the carboxylic acid is used as the acylating agent, it is preferred to carry out the reaction in the presence of a condensing agent, for example, dicyclohexylcarbodiimide, etc. Alternatively, where other acylating agents are used, the acylation is preferably carried out in the presence of a tertiary amine such as pyridine, triethylamine, etc. In either case, a solvent inert to the reaction (chloroform, dichloromethane, tetrahydrofuran, etc.) can also be safely present. The reaction time is about 0.5 to 5 hours and the reaction temperature is about 0° to 25° C.

The thus obtained compounds (II), (III) and (IV) can be isolated and purified by conventional known methods, for example, change of solvents, recrystallization, chromatography, etc. as described in Nozomi et al, "Busshitsu no Tanri to Seisei-tennen Seiri Kassei Bussitsu o chusin to shite" (Isolation and Purification of Substances-centered on naturally occuring physiologically active substances) Tokyo Daigaku Shuppankai (1976).

Examples of the non-toxic salts of the compounds of this invention (IV) wherein at least one of $R_6$, $R_9$ and $R_{10}$ contains a carboxyl group include alkali metal salts (sodium salts, potassium salts, lithium salts, etc.), alkaline earth metal salts (calcium salts, etc.), etc., of which the sodium salts and the potassium salts, are particularly preferred.

Specific examples of the preparation of the compounds of this invention are given below which are not construed as limiting the scope of this invention.

PREPARATION EXAMPLE 1: PREPARATION OF THE COMPOUND (II-1)

50 kg of cinnamon was treated with hot water at 60° to 100° C. for 1 to 2 hours, and the resultant extract was adsorbed onto 100 to 140 liters of the Amberlite XAD-2 resin.

After washing with water, the resin was eluted using a 40 to 80% methanol aqueous solution as an eluent; the eluted fraction thus obtained was concentrated under reduced pressure and freeze dried to afford 148 g of a crude powder. This crude powder was transferred to a silica gel column, and fractionation with preparative normal phase high performance liquid chromatography (HPLC) using a mixed solvent of chloroform-methanol-water (40–70:10:1) as a mobile phase solvent and that with preparative reversed phase HPLC on a $C_{18}$ column using a 6 to 10% aqueous acetonitrile solution as a mobile phase solvent were carried out successively and repeatedly using anti-ulcer activity as an index to give 19.35 mg of the compound (II-1) as a single component manifesting the activity most strongly.

The physical properties of the compound (II-1), i.e. 3,4,5-trimethoxyphenol-$\beta$-D-apiofranosyl-(1→6)-$\beta$-D-glucopyranoside were as follows:

Appearance: White amorphous powder $[\alpha]_D^{25}$: −99.8° (MeOH, C 0.5%)

UV (MeOH): $\lambda$max 212 nm (log$\epsilon$=3.96), 270 nm (log$\epsilon$=2.96)

IR (neat, cm$^{-1}$): 3400, 2960, 2870, 1605, 1510, 825, 785

$^1$H-NMR (MeOH-D$_4$, $\delta$ppm): 6.50 (2H, s), 4.96 (1H, d, J=2.7Hz), 4.80 (1H, dd, J=1.9, 5.7Hz), 4.06–4.03 (1H, m) 3.95 (1H, d, J=9.7Hz), 3.87 (1H, d, J=2.7Hz) 3.82 (6H, s), 3.74 (1H, d, J=9.7Hz), 3.70 (3H, s), 3.60–3.57 (2H, m), 3.54 (2H, s), 3.45–3.40 (3H, m)

$^{13}$C-NMR (MeOH-D$_4$, $\delta$ppm): 156.4(s), 155.3(s), 155.3(s), 135.2(s), 111.3(d), 103.7(d), 96.9(d), 96.9(d), 81.0(s), 78.4(d), 78.4(d), 77.5(d), 75.4(t), 75.4(d), 72.1(d), 69.2(t), 65.9(t), 61.7(q), 57.2(q), 57.2(q)

PREPARATION EXAMPLE 2: PREPARATION OF THE COMPOUND (II-2)

15 mg of the compound (II-1) and 10 mg of crude hesperidinase were incubated in 5 ml of distilled water at 40° C. for about 4 hours. The reaction mixture was concentrated under reduced pressure, and thereafter purified by fractionation by preparative reversed phase HPLC on a $C_{18}$ column using a 6 to 10% acetonitrile solution as a modile phase solvent to give 5 mg of the aglycone moiety, 3,4,5-trimethoxyphenol [compound (II-2)] as a pale yellow powder.

IR (KBr, cm$^{-1}$): 3600, 2960, 2950, 1600, 1505, 1460, 1370 1250, 1125, 1050, 870

$^1$H-NMR (MeOH-D$_4$, $\delta$ppm): 6.45 (2H, s), 3.85 (6H, s), 3.70 (3H, s)

PREPARATION EXAMPLE 3: PREPARATION OF AN AGLYCONE DERIVATIVE

A solution of 3 mg of the compound (II-2), 10.2 mg of 2,3,4,6-tetra-O-acetyl-$\alpha$-D-bromohexose and 7 mg of benzyltriethylammonium bromide in 5 ml of chloroform and 0.4 ml of a 1.25N aqueous sodium hydroxide solution was heated on an oil bath at 60° C. for about 3 hours. After completion of the reaction, the chloroform phase was concentrated, and purified and fractionated by preparative normal phase HPLC on a silica gel column using a mixed solvent of chloroform-methanol-water (40–70:10:1) as a mobile phase to afford 7.2 mg of a tetraacetylglycoside compound [compound II-6] of the formula given below wherein R is CH$_3$CO. Further, to a solution of this tetraacetylglucoside compound in 2 ml of a solution of dry ethanol-benzene (2:1) was added 4 mg of anhydrous potassium carbonate with ice cooling, stirred at room temperature for about 45 minutes, the reaction mixture was concentrated under reduced pressure, and purified and fractionated by preparative reversed phase HPLC on a $C_{18}$ column using a 6 to 10% aqueous acetonitrile solution as a mobile phase to obtain 4.1 mg of a monoglycoside compound [compound II-6] of the formula given below wherein R is H.

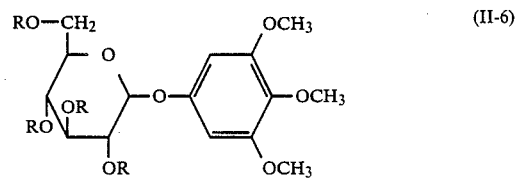

(II-6)

The physical properties of this monoglycoside compound were as follows:

IR (neat, cm$^{-1}$): 3400, 2950, 2850, 1610, 1500

$^1$H-NMR-D$_4$, δppm): 6.50 (2H, s), 4.80 (1H, d, J=5.9Hz), 4.05–4.00 (1H, m) 3.81 (6H, s), 3.68 (3H, s), 3.62–3.59 (2H, m), 3.50–3.45 (3H, m)

PREPARATION EXAMPLE 4: PREPARATION OF THE COMPOUND (III-1)

50 kg of cinnamon was treated with hot water at 60° to 100° C. for 1 to 2 hours, and the resultant extract was adsorbed onto 100 to 140 liters of the Amberlite XAD-2 resin. This resin was washed with water, then eluted using a 40 to 80% aqueous methanol solution as an eluent; the eluted fraction thus obtained was concentrated under reduced pressure and freeze dried to obtain 148 g of a crude powder. This crude powder was transferred to a silica gel column, and fractionation with preparative normal phase high performance liquid chromatography (HPLC) using a mixed solvent of chloroform-methanol-water (40–70:10:1) as a mobile phase solvent and that with preparative reversed phase HPLC on a C$_{18}$ column using a 6 to 10% acetonitrile aqueous solution as a mobile phase solvent were carried out successively and repeatedly using anti-ulcer activity as an index to obtain 41.05 mg of the compound (III-1), i.e. 2-(2-acetylvinylidene)-1,3,3-(trimethylcyclohexane-1,5-diol-5-O-β-D-apiofranosyl-(1→6)-β-D-glucopyranoside as a single peak component manifesting the activity most strongly.

The physical properties of the compound (III-1) were as follows:

Appearance: White amorphous powder $[\alpha]_D^{26}$: −88.6° (MeOH, C 0.5%)

UV(MeOH): λmax 231 nm (logε=4.07)

IR (neat, cm$^{-1}$): 3350, 2930, 1940, 1665, 1610, 864, 821

$^1$H-NMR (MeOH-D$_4$, δppm): 5.83 (1H, s), 5.00 (1H, d, J=2.4Hz), 4.42 (1H, d, J=7.9Hz), 4.31 (1H, m), 3.98 (2H, m), 3.89 (1H, d, J=2.4Hz), 3.77 (1H, d, J=9.7Hz), 3.62 (1H, dd, J=5.5, 11.4Hz), 3.58 (2H, s), 3.45–3.39 (1H, m), 3.36–3.25 (2H, m), 3.14 (1H, dd, J=7.9, 8.4Hz) 2.35 (1H, d, J=14.2Hz), 2.19 (3H, s), 1.52–1.43 (2H, m), 1.40 (3H, s), 1.39 (3H, s), 1.16 (3H, s)

$^{13}$C-NMR (MeOH-D$_4$, δppm): 211.9(s), 201.2(s), 120.8(s), 111.4(d). 103.6(d), 101.7(d), 81.0(s), 78.7(d), 78.7(d), 77.3(d), 75.7(d), 75.6(t), 73.7(d), 72.9(s), 72.4(d), 69.1(t), 66.6(t), 48.8(t), 47.4(t), 37.5(s), 32.8(q), 31.3(q), 30.0(q), 27.0(q)

PREPARATION EXAMPLE 5: PREPARATION OF THE COMPOUND (III-2)

20 mg of the compound (III-1) was dissolved in 2 ml of methanol and 2 ml of 2N hydrochloric acid, and reacted at 39° C. for about 6 hours. The reaction mixture was concentrated under reduced pressure, and purified and fractionated with preparative reversed phase HPLC on a C$_{18}$ column using a 6 to 10% aqueous acetonitrile solution as a mobile phase solvent to obtain 7.5 mg of the aglycone compound (III-2), i.e. 4-(2,4-dihydroxy-2,6,6-trimethylcyclohexylidene)-3-buten-2-one as a yellow oil.

IR (neat, cm$^{-1}$): 3620, 2920, 1945, 1670

$^1$H-NMR (MeOH-D$_4$, δppm, 200MHz): 5.80 (1H, s), 4.28 (1H, m), 2.40–2.10 (2H, m), 2.15 (3H, s), 1.50–1.45 (2H, m), 1.40 (3H, s), 1.36 (3H, s), 1.16 (3H, s)

PREPARATION EXAMPLE 6: PREPARATION OF AN AGLYCONE DERIVATIVE (GLUCOSIDE)

A solution of 4.5 mg of the compound (III-2), 12.5 mg of 2,3,4,6-tetra-O-acetyl-α-D-bromohexose and 8.5 mg of benzyltriethylammonium bromide in 5 ml of chloroform and 0.5 ml of 1.25N aqueous sodium hydroxide solution was heated at reflux on an oil bath at 60° C. for about 3 hours. After completion of the reaction, the chloroform phase was concentrated and purified and fractionated by preparative normal phase HPLC on a silica gel column using a mixed solvent of chloroform-methanol-water (40–70:10:1) as a mobile phase to obtain 9.6 mg of a tetraacetylglucoside compound. Further, 5 mg of anhydrous potassium carbonate was added to a solution of this acetyl compound in 2.5 ml of dry methanol-benzene (2:1) with ice cooling, stirred at room temperature for about 1.5 hours, then the reaction mixture was concentrated under reduced pressure, and purified and fractionated with preparative reversed phase HPLC on a C18 column using a 6 to 10% aqueous acetonitrile solution as a mobile phase solvent to obtain 5.7 mg of a monoglucoside compound in a white amorphous powder form.

The physical properties of this monoglucoside compound was as follows:

IR (neat, cm$^{-1}$): 3400, 2940, 1945, 1670, 1600

$^1$H-NMR (MeOH-D$_4$, δppm): 5.81 (1H, s), 4.40 (1H, d, J=8Hz), 4.29 (1H, m), 4.00 (1H, d, J=11.2Hz), 3.63 (1H, dd, J=5.2, 11.2Hz), 3.45–3.25 (3H, m), 3.15 (1H, dd, J=8, 8.4Hz), 2.35 (1H, d, J=14.1Hz), 2.18 (3H, s), 2.12 (1H, d, J=14.1Hz), 1.55–1.45 (2H, m), 1.40 (3H, s), 1.37 (3H, s), 1.16 (3H, s)

PREPARATION EXAMPLE 7: PREPARATION OF A HEPTAACETATE OF THE COMPOUND (III-1)

2 ml of acetic anhydride and 4 ml of pyridine were reacted with 12 mg of the compound (III-1) at room temperature for 30 minutes, the reaction mixture was concentrated under reduced pressure, and purified and fractionated with preparative normal phase HPLC on a silica gel column using a mixed solvent of chloroform-methanol-water (40–70:10:1) as a mobile phase to obtain 12.2 mg of a heptaacetate compound as a pale yellow oil.

IR (neat, cm$^{-1}$): 1490, 1750, 1670, 1600 (no OH absorption was observed).

$^1$H-NMR (MeOH-D$_4$, δppm): 2.00–2.07 (3H×7, s, Ac).

PREPARATION EXAMPLE 8: PREPARATION OF A HEPTAMETHYL ETHER OF THE COMPOUND (III-1)

25 mg of sodium hydride was stirred in 2 ml of dimethyl sulfoxide at 70° C. in nitrogen atmosphere for an hour, and thereafter cooled to room temperature. To this solution was added a solution of 8 mg of the compound (III-1) dissolved in 0.5 ml of dimethyl sulfoxide, stirred for an hour, then 0.1 ml of methyl iodide was added and further stirred for about 4 hours. To this reaction mixture was added about 5 ml of ice water and extraction was extracted twice with 3 ml portions of chloroform. The extract was concentrated, and purified and fractionated with the aforesaid preparative normal phase HPLC to obtain 7 mg of a yellow oil heptamethyl ether.

IR (neat, cm$^{-1}$): 1945, 1660, 1610, 1580 (no OH absorption was observed).

$^1$H-NMR (MeOH-D$_4$, δppm): 3.34–3.95 (3H×7, s, OMe)

PREPARATION EXAMPLE 9: ISOLATION OF THE COMPOUND (IV-1) (R$_1$=GLUCOSE, R$_2$=R$_3$=H)

200 kg of cinammon was treated with hot water at 60° to 100° C. for 1 to 2 hours, and the resultant extract was adsorbed onto 400 to 500 liters of the Amberlite XAD-2 resin. This resin was washed with water, then eluted with a 40 to 80% aqueous methanol solution as an eluent, the eluted fraction thus obtained was concentrated under reduced pressure and freeze-dried to obtain 590 g of a crude powder. This crude powder was subjected to fractionation with preparative normal phase high performance liquid chromatography (HPLC) on a silica gel column, using a mixed solvent of chloroform-methanol-water (40–70:10:1) as a mobile phase solvent and that with preparative reversed phase HPLC on a C$_{18}$ column using a 6 to 10% acetonitrile aqueous solution as a mobile phase solvent successively and repeatedly using anti-ulcer activity as an index, to obtain 20.80 mg of powder as a single peak component manifesting the activity most strongly.

The physical properties of 2,4-dimethyl-3-(4-hydroxy-3-hydroxymethyl-1-butenyl)-4-(β-D-glucopyranosyl)oxymethyl-2-cyclohexen-1-one:

Appearance: White amorphous powder [α]$_D^{26.5}$: −25.2° (CH$_3$OH, C 0.5%)

MS(m/z): 417 M+H$^+$

IR νmax (cm$^{-1}$): 3350, 2920, 1650, 1600

UV λmax (nm): 265 (logε=3.55)

$^1$H-NMR (D$_2$O)

| Chemical Shift (δ, ppm) | Multiplet | Proton Coupling Constant (J, Hz) | Number of Proton |
|---|---|---|---|
| 1.15 | s | | 3H |
| 1.78 | d. | 0.9 | 3H |
| 1.77 | triple d. | 5.5, 6.2, 13.2 | 1H |
| 2.26 | triple d. | 5.5, 10.2, 13.2 | 1H |
| 2.55–2.63 | triple d. × 2 | 5.5, 6.2, 10.2, 18.0 | 2H |
| 2.65 | triple d. | 5.9, 7.0, 8.3 | 1H |
| 3.24 | double d. | 7.9, 9.2 | 1H |
| 3.35 | double d. | 9.0, 9.7 | 1H |
| 3.42 | triple d. | 2.2, 6.0, 9.7 | 1H |
| 3.45 | double d. | 9.0, 9.1 | 1H |
| 3.65 | double d. × 2 | 7.0, 11.0 | 2H |
| 3.70 | double d. | 6.0, 12.2 | 1H |
| 3.72 | d. | 10.0 | 1H |
| 3.73 | double d. × 2 | 5.9, 11.0 | 2H |
| 3.80 | d. | 10.0 | 1H |
| 3.90 | double d. | 2.2, 12.3 | 1H |
| 4.38 | d. | 7.8 | 1H |
| 5.66 | double d. | 8.5, 16.3 | 1H |
| 6.29 | double t. | 1.0, 16.3 | 1H |

$^{13}$C—NMR (D$_2$O)

| Chemical Shift (δ, ppm) | Type of Carbon | Chemical Shift (δ, ppm) | Type of Carbon |
|---|---|---|---|
| 15.66 | CH$_3$ | 75.67 | CH |
| 23.32 | CH$_3$ | 78.38 | CH |
| 33.82 | CH$_2$ | 78.60 | CH |
| 36.03 | CH$_2$ | 78.85 | CH$_2$ |
| 42.40 | C | 105.50 | CH |
| 50.34 | CH | 131.46 | CH |
| 63.45 | CH$_2$ | 134.29 | C |
| 64.67 | CH$_2$ | 139.22 | CH |
| 64.67 | CH$_2$ | 164.63 | C |
| 72.41 | CH | 207.33 | C |

PREPARATION EXAMPLE 10: PREPARATION OF THE COMPOUND (IV-2) (R$^1$=R$^2$=R$^3$=H)

13.8 mg of the compound (IV-1) obtained in Preparation Example 9 was taken in some of round bottomed flask of 30 ml and dissolved in 2 ml of a citric acid-sodium citrate buffer (50 mM, pH 4.6), to which was added a solution of 344 mg (1.720 units) of β-D-glucosidase (Type 2) dissolved in 10 ml of a citric acid-sodium citrate buffer, 100 l of toluene was added portionwise, after which the flask was tightly stoppered, and incubated in an oven at 37° C. for 91 hours. The reaction mixture was adsorbed to 3 ml of C$_{18}$ resin, which was washed with water, then the eluate obtained by elution using 3 ml of MeOH as an eluent was concentrated on a rotary evaporator, and further purified and fractionated with preparative reversed phase HPLC on a C$_{18}$ column using an 8% aqueous acetonitrile solution as a mobile phase solvent. The fractionated solution was concentrated on a rotary evaporator to dryness, and dried in a vacuum desiccator overnight to obtain 5.90 mg of a colorless oil.

Appearance: Colorless oil [α]$_D^{28.5}$: +8.6° (CH$_3$OH, C 0.25%)

MS (m/z): 2.54 (M$^+$), 236, 224, 206, 191, 179

IR νmax (cm$^{-1}$): 3400, 2960, 2905, 1650, 1600, 1385, 1365, 1340, 1040, 980

UV λmax (nm): 286 (logε=3.98)

$^1$H-NMR (CDCl$_3$)

| Chemical Shift (δ, ppm) | Multiplet | Coupling Constant (J, Hz) | Number of Proton |
|---|---|---|---|
| 1.12 | s | | 3H |
| 1.75 | triple d. | 5.8, 6.4, 13.5 | 1H |
| 1.81 | d. | 1.0 | 3H |
| 2.17 | triple d. | 5.7, 10.0, 13.5 | 1H |
| 2.51–2.69 | triple d. × 2 | 5.7, 6.4, 10.0, 17.7 | 2H |
| 2.67 | triple d. | 6.0, 6.9, 8.3 | 1H |
| 3.43 | d. | 11.5 | 1H |
| 3.66 | double d. × 2 | 7.0, 11.1 | 2H |
| 3.75 | triple d. × 2 | 6.0, 11.1 | 2H |
| 3.76 | d. | 11.6 | 1H |
| 5.67 | double d. | 8.4, 16.3 | 1H |
| 6.28 | triple d. | 1.0, 16.3 | 1H |

$^{13}$C—NMR (CDCl$_3$)

| Chemical Shift (δ, ppm) | Type of Carbon | Chemical Shift (δ, ppm) | Type of Carbon |
|---|---|---|---|
| 15.47 | CH$_3$ | 64.49 | CH$_2$ |
| 22.94 | CH$_3$ | 70.38 | CH$_2$ |
| 33.21 | CH$_2$ | 131.25 | CH |
| 35.80 | CH$_2$ | 134.24 | C |
| 43.07 | C | 139.00 | CH |
| 50.14 | CH | 164.74 | C |
| 64.49 | CH$_2$ | 207.05 | C |

PREPARATION EXAMPLE 11: PREPARATION OF THE COMPOUND (IV) (R$_6$=R$_9$=R$_{10}$=COCH$_3$)

0.5 ml of acetic anhydride and 1 ml of pyridine were reacted upon 1.5 mg of the compound obtained in Preparation Example 10 at room temperature for 30 minutes, the reaction mixture was concentrated under reduced pressure, and purified and fractionated with preparative normal phase HPLC on a silica gel column using a mixed solvent of chloroform-methanol (50–100:10) as a mobile phase to obtain 2.1 mg of a colorless oil.

IR νmax (cm$^{-1}$): 2950, 2900, 1750, 1650, 1600 (no OH absorption was observed).

¹H-NMR (CD₃OD, δppm): 2.12 (s, 6H, 2×COCH₃) 2.17 (s, 3H, COCH₃)

PREPARATION EXAMPLE 12: PREPARATION OF THE COMPOUND (IV) ($R_6=R_9=R_{10}=CH_3$)

1.5 mg of the compound obtained in Preparation Example 10 was suspended in 1 ml of a 10% aqueous potassium hydroxide solution, then 2.5 mg of dimethyl sulfate acid was added portionwise while vigorously stirring in an ice bath, and thereafter heated under reflux for 30 minutes. After cooling, the reaction mixture was extracted twice with 3 ml portions of diethyl ether, and the extract was concentrated, and purified and fractionated with the aforesaid preparative normal phase HPLC to obtain 1.2 mg of a colorless oil.

IR max (cm⁻¹): 2940, 2905, 1650, 1600 (no OH absorption was observed)

¹H-NMR (CDCl₃, δppm): 3.50 (s, 6H, 2×OCH₃), 3.65 (s, 3H, OCH₃)

The therapeutic and prophylatic agents for peptic ulcers which contain the compound (I) or (II) of this invention are useful as therapeutic and prophylatic agents for ulcers in mammals (humans, horses, dogs, mice, rats etc.).

The therapeutic and prophylatic agents for peptic ulcers of this invention can be administered either orally or parenterally. In the case of oral administration, they are appropriately mixed with pharmaceutically acceptable additives (carriers, excipients, diluents etc.) and used as powders, tablets, capsules, troches, aqueous mixtures, syrups, granules etc. In the case of parenteral administration, they are used as injectable compositions for intravenous, intramuscular and subcutaneous injections, suppositories etc. in the form of an aqueous solution of a non-aqueous suspension. They are prepared by processes known to those skilled in the art as described in the Japanese Pharmacopeia.

Although the amount to be administered may vary depending on the severeness, body weight, age etc. of the patient, for a human adult, a dosage of 0.001 to 0.1 mg/kg per day is suitable, and this is administered in one to several doses.

The therapeutic and prophylatic agents for peptic ulcer which contain the compound (I) or (II) of this invention not only have extremely excellent effects to treat and prevent peptic ulcers but also are almost free from toxicity, and their pharmacological effects are manifested significantly. Thus, they are extremely useful as drugs for therapy and prophylaxis of ulcer.

Experimental methods conducted in order to confirm the pharmacological effect, acute toxicity, administration route etc. of the compound (I) or (II) or non-toxic salts thereof, as well as their results are illustrated below.

(Pharmacological Effect)
Experimental Methods
(1) Serotonin Induced Ulcer

Wister strain male rats (weighing 160 to 180 g) were used after one day's fasting. Serotonin creatinine sulfate (30 mg/ml) was subcutaneously administered to the rats on the back at a rate of 1 ml per kg of the body weight. The stomach was excised 5 hours after administration of serotonin, and the total area of hemorrhagic erosion was measured as an ulcer index. The test drug was intragastrically administered to the rats through an oral Zonde (probe) 30 minutes before administration of serotonin.

(2) Stress Ulcer

Wister strain male rats (weighing 230-250 g) were fasted for 2 days, then, while confined in a Tokyo University Pharmaceutics Laboratory model cage, they were immersed up to the xiphocosta and pulled up 6 hours later, to determine the ulcer index. That is, the rats were clubbed to death, the major axis of hemorrhagic erosion was measured, and the total was made the ulcer index. the test drug was intragastrically administered through an oral Zonde (probe) immediately before the loading of stress.

(3) Ethanol Induced Ulcer

Wister strain male rats (weighing 160-180 g) were fasted for one day and intragastrically administered with 50% (v/v) ethanol at a rate of 1 ml per rat. The test drug was intragastirically administered through an oral Zonde (probe) 30 minutes before administration of ethanol. One hour after administration of ethanol, the rats were poisoned to death by inhalation of chloroform, each stomach was excised, the major axis of hemorrhagic erosion on the stomach part was measured, and the total was made an ulcer index.

| Ulcer Model | Sample | Amount Administered (μg/kg) | Ulcer Index* | Rate of Inhibition |
|---|---|---|---|---|
| Serotonin Induced Ulcer | Control | — | 17.5 ± 5.5 | — |
| | Compound (II-1) | 0.15 | 7.5 ± 2.3 | 57.1 |
| | Compound (II-1) | 0.30 | 5.1 ± 1.9 | 70.9 |
| | Control | — | 20.6 ± 5.7 | — |
| | Compound (II-2) | 0.05 | 15.1 ± 4.6 | 26.7 |
| | Compound (II-2) | 0.15 | 11.2 ± 2.4 | 45.6 |
| | Contol | — | 17.5 ± 5.5 | — |
| | Compound (III-1) | 0.075 | 17.0 ± 3.1 | 2.9 |
| | Compound (III-1) | 0.15 | 4.3 ± 1.1 | 75.4 |
| | Control | — | 13.4 ± 2.1 | — |
| | Compound (IV-1) | 0.1 | 7.1 ± 3.4 | 47.0 |
| | Compound (IV-1) | 1 | 6.5 ± 2.5 | 51.5 |
| | Compound (IV-2) | 0.06 | 4.6 ± 1.2 | 65.7 |
| | Compound (IV-2) | 6 | 3.1 ± 1.2 | 76.9 |
| Stress Ulcer | Control | — | 28.3 ± 5.7 | — |
| | Compound (II-1) | 0.15 | 21.6 ± 5.8 | 23.7 |
| | Compound (II-1) | 0.30 | 11.7 ± 3.0 | 58.5 |
| | Control | — | 28.3 ± 5.7 | — |
| | Compound (III-1) | 0.075 | 16.6 ± 3.2 | 41.3 |
| | Compound (III-1) | 0.15 | 9.4 ± 2.3 | 66.8 |
| Ethanol Induced Ulcer | Control | — | 51.0 ± 11.9 | — |
| | Compound (II-1) | 0.15 | 45.3 ± 14.0 | 11.1 |
| | Compound (II-1) | 0.30 | 27.0 ± 7.4 | 47.1 |
| | Control | — | 51.0 ± 11.9 | — |
| | Compound (III-1) | 0.075 | 24.7 ± 10.6 | 51.6 |
| | Compound (III-1) | 0.15 | 22.2 ± 8.1 | 56.5 |

Each numeral in the table indicates the mean ± standard error (n=8)

All the test drugs (compounds of this invention) were intragastrically administered by an oral Zonde (probe).

In the acute toxicity experiment on the compounds of this invention using ddy male mice, there was not observed toxicity which leads the animal to death even at a dose of 1 ml/kg-body weight, which is equivalent to about 3,000 times in the case of the compound (II), about 6,000 times in the case of the compound (III) and about 10,000 times in the case of the compound (IV) as compared with the effective dosage on the animal by intraperitoneal administration.

| Example 1: Tablets | | |
|---|---|---|
| (1) | Compound (I) | 0.5 mg |
| (2) | Fine granules for direct tabletting No. 209 (produced by Fuji Chemical Co.) | 46.6 mg |
| | Magnesium metaaluminosilicate | 20% |
| | Corn starch | 30% |
| | Lactose | 50% |
| (3) | Crystalline cellulose | 24.0 mg |
| (4) | Potassium carboxymethylcellulose | 4.0 mg |
| (5) | Magnesium stearate | 0.4 mg |

(1), (3) and (4) were passed through a 100-mesh sieve beforehand respectively. Then (1), (3), (2) and (4) were dried to reduce the water contents to the predetermined values respectively, and mixed at the abovedescribed weight proportion. To the mixed powder thus homogeneously mixed was added (5), mixed for a short time (30 seconds), and the mixed powder was tabletted (pestle: 6.3mmφ, 6.0 mmR) to obtain tablets each containing 75.5 mg.

These tablets may be coated wth gastric film coating agents (e.g. polyvinyl acetal diethylamino acetate), edible coloring agents etc. which are conventionally employed, if desired.

| Example 2: Capsules | |
|---|---|
| (1) Compound (I) | 2.5 g |
| (2) Lactose | 935 g |
| (3) Magnesium stearate | 15 g |

The above ingredients were weighed, homogeneously mixed and the mixed powder was filled into hard gelatin capsules 190 mg in each.

| Example 3: Injectable Composition | |
|---|---|
| (1) Compound (I) | 0.5 mg |
| (2) Glucose | 100 mg |
| (3) Physiological saline | 10 ml |

The above liquid mixture was filtered through a membrane filter, further filtered for sterilization, and the filtrate was allotted aseptically into vials, which were then filled with nitrogen gas and thereafter sealed to give an intravenously injectable composition.

EXAMPLE 4

Tablets, capsules and an injectable composition were obtained in manners similar to those in Examples 1, 2 and 3 respectively except that the compound (I) was replaced by the compound (II).

While the invention has been described in detail and with reference to specific embodiments thereof, it will be apparent to one skilled in the art that various changes and modifications can be made therein without departing fromn the spirit and scope thereof.

What is claimed is:

1. A therapeutic and prophylactic agent for peptic ulcer which comprises as an active ingredient, in substantially pure isolated form, at least one member selected from the group consisting of a compound of the general formula (I):

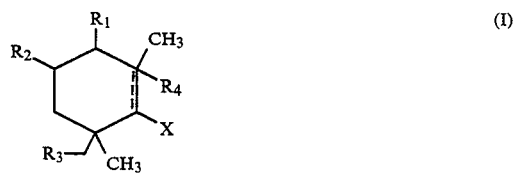

wherein $R_1$ represents hydrogen or $=O$; $R_2$ represents hydrogen or $-OR_5$; $R_3$ represents hydrogen or $-OR_6$; $R_4$ represents $-OR_7$ in the case of the absence of double bond; $R_5$, $R_6$ and $R_7$ each represents hydrogen or an organic residue;

X represents group (A):

or group (B):

wherein $R_8$ represents alkyl, and $R_9$ and $R_{10}$ each represents hydrogen or an organic residue; with the proviso that when X represents group (A), then $R_1$ and $R_3$ both represent hydrogen, $R_2$ represents $-OR_5$, $R_4$ represents $OR_7$ and the bond between the carbon atom to which X is attached and the carbon atom to which $R_4$ is attached is a single bond, and when X represents group (B), then $R_1$ represents $=O$, $R_2$ represents hydrogen, $R_3$ represents $-OR_6$ and the bond between the carbon atom to which X is attached and the carbon atom to which $R_4$ is attached is a double bond, or a pharmaceutically acceptable salt thereof; and a compound of the general formula (II):

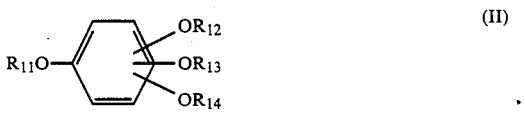

wherein $R_{11}$ represents hydrogen or an organic residue, and $R_{12}$, $R_{13}$ and $R_{14}$ each represents an organic residue; or a pharmaceutically acceptable salt thereof and a pharmaceutically acceptable carrier, wherein each of said organic residues for $R_5$, $R_6$, $R_9$ and $R_{10}$ independently represents straight-chain or branched-chain alkyl of 1 to 6 carbon atoms, aliphatic or aromatic acyl of 1 to 6 carbon atoms, alkoxycarbonyl having a straight-chain alkoxy moiety of 1 to 6 carbon atoms and a straight-chain or branched-chain alkyl moiety of 1 to 6 carbon atoms, carboxyalkyl having a straight-chain or branched-chain alkyl moiety of 1 to 6 carbon atoms, carboxyalkylcarbonyl having a straight-chain or branched-chain alkyl moiety of 1 to 6 carbon atoms, cyclic acetal or an oligosaccharide residue of 1 to 3 saccharide units in which the hydroxyl groups are substituted or unsubstituted, and wherein the organic residue for $R_{11}$ represents straight-chain or branched-chain alkyl of 1 to 6 carbon atoms, aliphatic or aromatic acyl of 1 to 6 carbon atoms, alkoxycarbonyl having a straight-chain or branched-chain alkoxy moiety of 1 to 6 carbon atoms, alkoxycarbonylalkyl having a straight-chain or branched-chain alkoxy moiety of 1 to 6 carbon atoms and a straight-chain or branched-chain alkyl moiety of 1 to 6 carbon atoms, carboxyalkylcarbonyl having a straight-chain or branched-chain alkyl moiety of 1 to 6 carbon atoms or an oligosaccharide residue of 1 to 3 saccharide units in which the hydroxyl groups are substituted or unsubstituted, and wherein each of said organic residues for $R_{12}$, $R_{13}$ and $R_{14}$ independently represents straight-chain or branched-chain alkyl of 1 to 6 carbon atoms, alkoxycarbonyl having a straight-chain or branched-chain alkoxy moiety of 1 to 6 carbon atoms, alkoxycarbonylalkyl having a straight-chain or branched-chain alkoxy moiety of 1 to 6 carbon atoms and a straight-chain or branched-chain alkyl moiety of 1 to 6 carbon atoms, carboxyalkyl having a straight-chain or branched-chain alkyl moiety of 1 to 6 carbon atoms or carboxyalkylcarbonyl having a straight-chain or branched-chain alkyl of 1 to 6 carbon atoms, and wherein the organic residue for $R_7$ is straight-chain or branched-chain alkyl of 1 to 6 carbon atoms, aliphatic or aromatic acyl of 1 to 6 carbon atoms, alkoxycarbonyl having a straight-chain or branched-chain alkoxy moiety of 1 to 6 carbon atoms, alkoxycarbonylalkyl having a straight-chain or branched-chain alkoxy moiety of 1 to 6 carbon atoms and a straight-chain or branched-chain alkyl moiety of 1 to 6 carbon atoms, carboxyalkyl having a straight-chain or branched-chain alkyl moiety of 1 to 6 carbon atoms, carboxyalkylcarbonyl having a straight-chain or branched-chain alkyl moiety of 1 to 6 carbon atoms or cyclic acetal.

2. The therapeutic and prophylactic agent for peptic ulcers according to claim 1, wherein at least one of $R_6$, $R_9$ and $R_{10}$ in the above general formula (I) contains a carboxyl group, and forms at least one nontoxic salt selected from a sodium salt, a potassium salt, a lithium salt and a calcium salt.

3. The therapeutic and prophylactic agent for peptic ulcers according to claim 1, wherein the compound of the general formula (I) is a terpene derivative of the general formula (III):

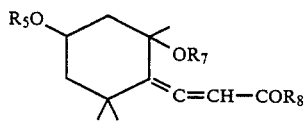

(III)

whrein $R_5$, $R_7$ and $R_8$ are as defined above under the general formula (I).

4. The therapeutic and prophylactic agent for peptic ulcers according to claim 1, wherein the compound of the general formula (I) is a terpene derivative of the general formula (IV):

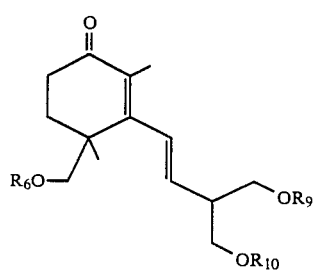

(IV)

wherein $R_6$, $R_9$ and $R_{10}$ are as defined above under the general formula (I).

5. An isolated compound of the general formula (I):

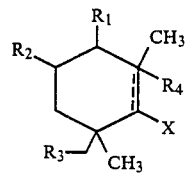

(I)

wherein $R_1$ represents hydrogen or =O, $R_2$ represents hydrogen or $-OR_5$; $R_3$ represents hydrogen or $-OR_6$; $R_4$ represents $-OR_7$ in the case of the absence of double bond; $R_5$, $R_6$ and $R_7$ each represents hydrogen or an organic residue;

X represents group (A):

(A)

or group (B):

(B)

wherein $R_8$ represents alkyl, and $R_9$ and $R_{10}$ each represents hydrogen or an organic residue; with the proviso that when X represents group (A), then $R_1$ and $R_3$ both represent hydrogen, $R_2$ represents $-OR_5$, $R_4$ represents $OR_7$ and the bond between the carbon atom to which X is attached and the carbon atom to which $R_4$ is attached is a single bond, and when X represents group (B), then $R_1$ represents =O, $R_2$ represents hydrogen, $R_3$ represents $-OR_6$ and the bond between the carbon atom to which X is attached and the carbon atom to which $R_4$ is attached is a double bond, or a nontoxic salt thereof and wherein each of said organic residues for $R_5$, $R_6$, $R_9$ and $R_{10}$ independently represents straight-chain or branched-chain alkyl of 1 to 6 carbon atoms, aliphatic or aromatic acyl of 1 to 6 carbon atoms, alkoxycarbonyl having a straight-chain or branched-chain alkoxy moiety of 1 to 6 carbon atoms, alkoxycarbonylalkyl having a straight-chain or branched-chain alkoxy moiety of 1 to 6 carbon atoms and a straight-chain or branched-chain alkyl moiety of 1 to 6 carbon atoms, carboxyalkyl having a straight-chain or branched-chain alkyl moiety of 1 to 6 carbon atoms, carboxyalkylcarbonyl having a straight-chain or branched-chain alkyl moiety of 1 to 6 carbon atoms, cyclic acetal or an oligosaccharide residue residue of 1 to 3 saccharide units in which the hydroxyl groups are substituted or unsubstituted and wherein the organic residue for $R_7$ represents a straight-chain or branched-chain alkyl of 1 to 6 carbon atoms, aliphatic or aromatic acyl of 1 to 6 carbon atoms, alkoxycarbonyl having a straight-chain or branched-chain alkoxy moiety of 1 to 6 carbon atoms, alkoxycarbonylalkyl having a straight-chain or branched-chain alkoxy moiety of 1 to 6 carbon atoms and a straight-chain or branched-chain alkyl moiety of 1 to 6 carbon atoms, carboxyalkyl having a straight-chain or branched-chain alkyl moiety of 1 to 6 carbon atoms, carboxyalkylcarbonyl having a straight-chain or branched-chain alkyl moiety of 1 to 6 carbon atoms or cyclic acetal.

6. The compound according to claim 5, which is of the general formula (I) wherein at least one of $R_6$, $R_9$ and $R_{10}$ contains a carboxyl groups, and forms a sodium salt, a potassium salt, a lithium salt or a calcium salt.

7. The compound according to claim 5, which is of the general formula (I) wherein X represents group (A) and which is of the general formula (III):

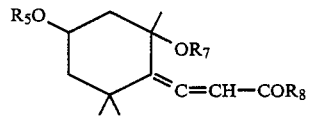

wherein $R_5$, $R_7$ and $R_8$ are as defined above under the general formula (I).

8. The compound according to claim 5, which is of the general formula (I) wherein X represents a group (B) and which is of the general formula (IV):

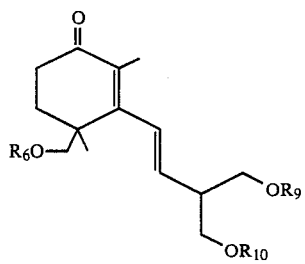

wherein $R_6$, $R_9$ and $R_{10}$ are as defined above under the general formula (I).

9. A method of administering to a host the therapeutic and prophylactic agent for peptic ulcers according to claim 1 which comprises administering to said host said compound of general formula (I) or (II) in an amount of from 0.001 to 0.1 mg/kg per day.

* * * * *